(12) United States Patent
Porter et al.

(10) Patent No.: US 7,323,596 B2
(45) Date of Patent: Jan. 29, 2008

(54) ANTIMICROBIAL AGENTS

(75) Inventors: Barry Porter, Cambridge (GB); Paul Gane, Cambridge (GB); Raymond Beckett, Oxford (GB); Kenneth Keavey, Oxford (GB); Jac Wijkmans, Oxford (GB); Lydia Saroglou, Oxford (GB)

(73) Assignee: De Novo Pharmaceuticals Ltd. (GB)

( * ) Notice: Subject to any disclaimer, the term of this patent is extended or adjusted under 35 U.S.C. 154(b) by 723 days.

(21) Appl. No.: 10/433,625

(22) PCT Filed: Dec. 21, 2001

(86) PCT No.: PCT/GB01/05732

§ 371 (c)(1),
(2), (4) Date: Dec. 30, 2003

(87) PCT Pub. No.: WO02/50081

PCT Pub. Date: Jun. 27, 2002

(65) Prior Publication Data

US 2004/0102491 A1 May 27, 2004

(30) Foreign Application Priority Data

Dec. 21, 2000 (GB) ................... 0031223.1
Nov. 24, 2001 (GB) ................... 0128234.2

(51) Int. Cl.
*C07C 239/00* (2006.01)
*C07C 259/00* (2006.01)
*C07C 303/00* (2006.01)
*C07C 307/00* (2006.01)
*C07C 309/00* (2006.01)
*C07C 311/00* (2006.01)

(52) U.S. Cl. .................. 564/300; 564/301; 564/80; 564/84; 564/90; 564/92; 564/93

(58) Field of Classification Search ........... 564/80–99, 564/300–301
See application file for complete search history.

(56) References Cited

FOREIGN PATENT DOCUMENTS

WO   WO 9108737 A   *  6/1991
WO   WO 00 35440 A      6/2000

OTHER PUBLICATIONS

Scozzafava: "Protease inhibitors part 12" Eur. J. Pharm.Sci., vol. II, Jul. 2000, pp. 69-79, XP000971120 Table 2 Discussion about lead compound 4, p. 75, left-hand column, p. 71, left hand column, paragraph 1.

Scozzafava A et al: "Protease inhibitors—Part 5. Alkyl/arylsulfonyl—and arylsulfonylureido-/arylureido-glycine hydroxamate inhibtors of *Clostridium histolyticum* collagenase" European Journal of Medicinal Chemistry, Editions Scientifieuqe Elsevier, Paris, FR, vol. 35, No. 3, Mar. 2000, pp. 299-307, XP004341234 ISSN 0223-5234 Table 1 last 7 lines, p. 300, left-hand column.

Broughton et al: "Studies concerning the Antibiotic Actinonin" Journal of the Chemical Society, Perkin Transactions 1, Chemical Society. Letchworth, GB, vol. 9, 1975, pp. 857-860, XP002157880, ISSN: 1472-7781, cited in the application example 21.

* cited by examiner

*Primary Examiner*—Sreeni Padmanabhan
*Assistant Examiner*—Kendra D. Carter
(74) *Attorney, Agent, or Firm*—Banner & Witcoff, Ltd.

(57) ABSTRACT

Compounds of formula (I) and (IA) have antibacterial or antiprotozoal activity: formula (1) formula (2) wherein: Z represents a radical of formula $N(OH)CH(=O)$ or of formula $C(=O)NH(OH)$; $R_1$ represents hydrogen, methyl or trifluoromethyl, or, except when Z is a radical of formula $N(OH)CH(=O)$, a hydroxy or amino group; $R_2$ represents a radical of formula $R_{10}-(X)_n-(ALK)_m-$ wherein $R_{10}$ represents hydrogen, or an optionally substituted $c_1$-$C_6$ alkyl, $C_2$-$C_6$ alkenyl, $C_2$-$C_6$ alkynyl, cycloalkyl, aryl, or heterocyclyl group, ALK represents a straight or branched divalent $C_1$-$C_6$ alkylene, $C_2$-$C_¿6$ ?alkenylene, or $C_2$-$C_6$ alkynylene radical, and may be interrupted by one or more non-adjacent NH—, —O— or S— linkages, X represents NH—, —O— or S—, and m and n are independently 0 or 1; $R_3$ represents hydrogen, $C_1$-$C_6$alkyl, or benzyl; and $R_4$ is as defined in the specification.

9 Claims, No Drawings

ANTIMICROBIAL AGENTS

This application is a U.S. National Stage application of co-pending PCT application PCT/GB01/05732 filed Dec. 21, 2001, which claims the priority of United Kingdom Patent Application No. 0128234.2, filed Nov. 24, 2001, which claims the priority of United Kingdom Patent Application No. 0031223.1, filed Dec. 21. 2000. These applications are incorporated herein by reference in there entireties.

This invention relates to the use of hydroxamic acid and N-formyl hydroxylamine derivatives as antibacterial and antiprotozoal agents, to novel compounds within those classes, and to pharmaceutical and veterinary compositions comprising such compounds.

BACKGROUND OF THE INVENTION

In general, bacterial pathogens are classified as either Gram-positive or Gram-negative. Many antibacterial agents (including antibiotics) are specific against one or other Gram-class of pathogens. Antibacterial agents effective against both Gram-positive and Gram-negative pathogens are therefore generally regarded as having broad spectrum activity.

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes.

Amongst the Gram-positive pathogens, such as *Staphylococci, Streptococci, Mycobacteria* and *Enterococci*, resistant strains have evolved/arisen which makes them particularly difficult to eradicate. Examples of such strains are methicillin resistant *Staphylococcus aureus* (MRSA), methicillin resistant coagulase negative *Staphylococci* (MRCNS), penicillin, quinolone or macrolide resistant *Streptococcus pneumoniae* and multiply resistant *Enterococcus faecium*.

Pathogenic bacteria are often resistant to the aminoglycoside, β-lactam (penicillins and cephalosporins), macrolide, quinolone and chloramphenicol types of antibiotic. The mechanism of resistance can involve the enzymatic inactivation of the antibiotic by hydrolysis, formation of inactive derivatives, mutation of the molecular target and/or activation of transport pumps. The β-lactam (penicillin and cephalosporin) family of antibiotics are characterised by the presence of a β-lactam ring structure. Resistance to this family of antibiotics in clinical isolates is most commonly due to the production of a "penicillinase" (β-lactamase) enzyme by the resistant bacterium which hydrolyses the β-lactam ring thus eliminating its antibacterial activity.

Recently there has been an emergence of vancomycin-resistant strains of *enterococci* (Woodford N. 1998 Glycopeptide-resistant *enterococci*: a decade of experience. Journal of Medical Microbiology. 47(10):849-62). Vancomycin-resistant *enterococci* are particularly hazardous in that they are frequent causes of hospital based infections and are inherently resistant to most antibiotics. Vancomycin works by binding to the terminal D-Ala-D-Ala residues of the cell wall peptidoglycan precursor. The high-level resistance to vancomycin is known as VanA and is conferred by genes located on a transposable element which alter the terminal residues to D-Ala-D-lac thus reducing the affinity for vancomycin.

In view of the rapid emergence of multidrug-resistant bacteria, the development of antibacterial agents with novel modes of action that are effective against the growing number of resistant bacteria, particularly the vancomycin resistant *enterococci* and βlactam antibiotic-resistant bacteria, such as methicillin-resistant *Staphylococcus aureus*, is of utmost importance.

BRIEF DESCRIPTION OF THE INVENTION

This invention is based on the finding that certain hydroxamic acid and N-formyl hydroxylamine derivatives have antibacterial and antiprotozoal activity, and makes available new antibacterial and antiprotozoal agents. The compounds with which this invention is concerned are antibacterial with respect to a range of Gram-positive and Gram-negative organisms. They are characterised by the presence in the molecules of a backbone structure of formula (IB)

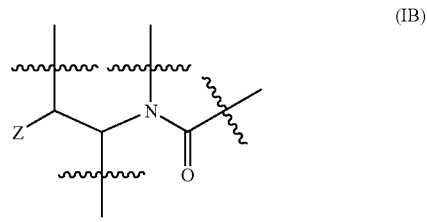

(IB)

in which Z is a hydroxamic acid or N-formyl hydroxylamine group and to which backbone a variety of substituent moieties are attached via the bonds shown as intersected by wavy lines.

Although it may be of interest to establish the mechanism of action of the compounds with which the invention is concerned, it is their ability to inhibit bacterial growth that makes them useful. However, it is presently believed that their antibacterial activity is due, at least in part, to intracellular inhibition of bacterial polypeptide deformylase (PDF; EC 3.5.1.31).

All ribosome-mediated synthesis of proteins starts with a methionine residue. In prokaryotes, the methionyl moiety carried by the initiator tRNA is N-formylated prior to its incorporation into a polypeptide. Consequently, N-formyl-methionine is always present at the N-terminus of a nascent bacterial polyleptide. However, most mature proteins do not retain the N-formyl group or the terminal methionine residue. Deformylation is required prior to methionine removal, since methionine aminopeptidase does not recognise peptides with an N-terminal formylmethionine residue (Solbiati et al., J. Mol. Biol. 290:607-614, 1999). Deformylation is, therefore, a crucial step in bacterial protein biosynthesis and the enzyme responsible, PDF, is essential for normal bacterial growth. The gene encoding PDF (def) is present in all pathogenic bacteria for which sequences are known (Meinnel et al., J. Mol. Biol, 266:93949, 1997). Although a deformylase homologue has recently been cloned from the mitochondria of human cells (Giglione et. el. EMBO Journal, 19, 5916-5929, 2000) it has not been shown to be functional, and its relevance is unknown. Since a number of currently used antibiotics are known to act on both bacteria and mitochondria, PDF is still considered to be a target for antibacterial chemotherapy (for a review see Giglione et al., Mol Microbiol., 36:1197-1205, 2000).

The isolation and characterisation of PDF has been facilitated by an understanding of the importance of the metal ion in the active site (Groche et al., Biophys. Biochem. Res. Commun., 246:324-6,1998). The $Fe^{2+}$ form is highly active in vivo but is unstable when isolated due to oxidative degradation (Rajagopalan et al., J. Biol. Chem. 273:22305-10,1998). The $Ni^{2+}$ form of the enzyme has specific activity comparable with the ferrous enzyme but is oxygen-insensitive (Ragusa et al., J. Mol. Biol. 1998, 280:515-23, 1998). The $Zn^{2+}$ enzyme is also stable but is almost devoid of catalytic activity (Rajagopalan et al., J. Am. Chem. Soc. 119:12418-12419, 1997).

Several X-ray crystal structures and NMR structures of *E. coli* PDF, with or without bound inhibitors, have been published (Chan et al., Biochemistry 36:13904-9, 1997; Becker et al., Nature Struct. Biol. 5:1053-8,1998; Becker et al., J. Biol. Chem. 273:11413-6,1998; Hao et al., Biochemistry, 38:4712-9, 1999; Dardel et al., J. Mol. Biol. 280:501-13, 1998; O'Connell et al., J. Biomol. NMR, 13:311-24, 1999), indicating similarities in active site geometry to metalloproteinases such as thermolysin and the metzincins.

The substrate specificity of PDF has been extensively studied (Ragusa et al., J. Mol. Biol. 289:1445-57,1999; Hu et al., Biochemistry 38:643-50,1999; Meinnel et al., Biochemistry, 38:4287-95, 1999). These authors conclude that an unbranched hydrophobic chain is preferred at P1', while a wide variety of P2' substituents are acceptable and an aromatic amide substituent may be advantageous at the P3' position. There have also been reports that small peptidic compounds containing an H-phosphonate (Hu et al., Bioorg. Med. Chem. Left., 8:2479-82, 1998) or thiol (Meinnel et al., Biochemistry, 38:4287-95, 1999; Huntingdon et al., Biochemistry, 39: 4543-51, 2000; Wei et al, J. Combinatorial Chem., 2: 650-57, 2000) metal binding group are micromolar inhibitors of PDF. Peptide aldehydes such as calpeptin (N-Cbz-Leu-norleucinal) have also been shown to inhibit PDF (Durand et al., Arch. Biochem. Biophys., 367:297-302, 1999). Recently, the naturally occurring hydroxamic acid antibiotic actinonin, for which the target of its antibacterial activity was previously unknown, was shown to be a potent inhibitor of polypeptide deformylase (WO 99/39704, and Chen et al, Biochemistry, 39: 1256-62, 2000). Examples of non-peptidic PDF inhibitors with carboxylic acid (Green et al., Arch. Biochem. Biophys. 375: 355-8, 2000; Jayasekera et al., ibid., 381:313-6, 2000) or hydroxamic acid (Apfel et al., J. Med. Chem., 43: 2324-31, 2000) metal binding groups are also known.

It has been reported that PDF is present in eukaryotic parasites such as *Plasmodium falciparum* (Meinnel, Parasitology Today, 16: 165-8, 2000). Those authors also found evidence for the presence of PDF in other parasites of humans, such as the kinetoplastid protozoan parasites *Trypanosoma brucei* and *Leishmania major*. Based on these findings, it is anticipated that the hydroxamic acid and N-formyl hydroxylamine compounds with which this invention is concerned have antiprotozoal activity, and are useful in the treatment of malaria and other protozoal diseases.

Several N-formyl hydroxylamine derivatives have previously been disclosed. The pharmaceutical utility ascribed to them is usually the ability to inhibit matrix metalloproteinases (MMPs) and in some cases release of tumour necrosis factor (TNF), and hence the treatment of diseases or conditions mediated by those enzymes, such as cancer and rheumatoid arthritis. Also, WO 97/38705 (Bristol-Myers Squibb) and a recent publication (Robl et al., Bioorg. Med. Chem. Lett., 10: 257-60, 2000) disclose certain N-formyl hydroxylamine derivatives as enkephalinase and angiotensin converting enzyme inhibitors. Furthermore, patent publications WO 99/41232 (British Biotech) and WO 00/43001 (British Biotech) respectively disclose the use of certain N-formyl hydroxylamine derivatives as inhibitors of proliferation of rapidly dividing cells and in the treatment of inflammation.

U.S. Pat. No. 4,738,803 (Roques et al.) also discloses N-formyl hydroxylamine derivatives as enkephalinase inhibitors and they are proposed for use as antidepressants and hypotensive agents.

Of the publications referred to above, it appears only U.S. Pat. No. 4,738,803 (Roques et al.) discloses N-formyl hydroxylamine derivatives of the type with which this invention is concerned, ie having a molecular backbone of formula (IA) above.

Very many hydroxamic acid derivatives are known. Many have been disclosed as having matrix metalloproteinase (MMP) inhibitory activity, and thus to be potentially useful for the treatment of diseases mediated by MMPS, for example cancer, arthritides, and conditions involving tissue remodelling such as wound healing, and restenosis. Others have been disclosed as inhibitors of other metalloenzymes such as enkephalinase, angiotensin converting enzyme and TNF converting enzyme. Publications relating to such hydroxamic acid derivatives include some which disclose hydroxamic acid compounds having the characteristic backbone structure (IA) of the compounds with which this invention is concerned. Such publications include the following:

| | |
|---|---|
| US-A-4,738,803 | (Roques et al.) |
| WO 91/08737 | (Fisons) |
| EP-A-0513810 | (Searle/Monsanto) |
| WO 96/39385 | (Pfizer) |
| WO 97/20824 | (Agouron) |
| WO 99/06041 | (Celgene) |
| WO 99/06340 | (Procter & Gamble) |
| WO 99/19296 | (Ono) |
| WO 00/59865 | (Ono) |
| Fournie-Zaluski et. al. Int. J. Pept. Protein Res. (1989), 33(2), 146-53 | |
| Burrell et. al. Clin. Sci. (1997), 93(1), 43-50. | |

Notwithstanding publications such as those mentioned above which disclose certain compounds of the type with which this invention is concerned, it appears none have recognised or taught the use of th present compounds as antibacterial or antiprotozoal agents. Furthermore, it appears some of the compounds with which this invention is concerned are novel per se, particularly the N-formyl hydroxylamines.

Actinonin is a naturally occurring antibacterial agent having a hydroxamic acid group, and certain derivatives of actinonin are also known to have. antibacterial activity. (see for example Bouboutou et al, Colloq. INSERM (1989)174 (Forum Pept. $2^{nd}$, 19, 3414; Lelevre et. al. Pathol. Biol. (1989), 37(1), 4346; Broughton et. al. J. Chem. Soc. Perkin Trans. 1 (1975) (9), 857-60). In the latter publication, an analogue of actinonin with the central amide linkage reversed was synthesised (compound 21, Table 2, page 859) but it lacked antibacterial activity. Our copending International patent applications nos. WO 99/39704, WO 99/59568, WO 00/35440, WO 00/44373, WO 00/58294 and WO 00/61134 disclose that certain N-formyl hydroxylamine and hydroxamic acid derivatives have antibacterial activity. With the single exception of compound 21 of Broughton et. al. mentioned above, the compounds with which these publications are concerned do not have the characterising backbone (IA) of the present compounds.

DETAILED DESCRIPTION OF THE INVENTION

According to the first aspect of the present invention there is provided the use of a compound of formula (I) or (IA) or a pharmaceutically or veterinarily acceptable salt, hydrate or solvate thereof in the preparation of a composition for treatment of bacterial or protozoal infections in humans and non-human mammals:

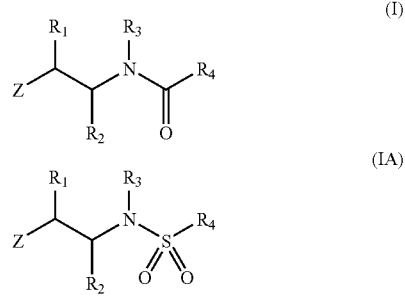

wherein:
Z represents a radical of formula —N(OH)CH(=O) or of formula —C(=O)NH(OH);
$R_1$ represents hydrogen, methyl or trifluoromethyl, or, except when Z is a radical of formula —N(OH)CH(=O), a hydroxy or amino group;
$R_2$ represents a radical of formula $R_{10}$—$(X)_n$-$(ALK)_m$- wherein
$R_{10}$ represents hydrogen, or a $C_1$-$C_6$ alkyl, $C_2$-$C_6$ alkenyl, $C_2$-$C_6$ alkynyl, cycloalkyl, aryl, or heterocyclyl group, any of which may be unsubstituted or substituted by $(C_1$-$C_6)$alkyl, $(C_1$-$C_6)$alkoxy, hydroxy, mercapto, $(C_1$-$C_6)$alkylthio, amino, halo (including fluoro, chloro, bromo and iodo), trifluoromethyl, cyano, nitro, oxo, —COOH, —CONH$_2$, —COOR$^A$, —NHCOR$^A$, —NR$^A$COR$^B$, —CONHR$^A$, —NHR$^A$, —NR$^A$R$^B$, or —CONR$^A$R$^B$ wherein R$^A$ and R$^B$ are independently a $(C_1$-$C_6)$alkyl group or R$^A$ and R$^B$ taken together with the atom(s) to which they are attached form a 5, 6 or 7 membered ring and
ALK represents a straight or branched divalent $C_1$-$C_6$ alkylene, $C_2$-$C_6$ alkenylene, or $C_2$-$C_6$ alkynylene radical, and may be interrupted by one or more non-adjacent —NH—, —O— or —S— linkages,
X represents —NH—, —O— or —S—, and
m and n are independently 0 or 1;
$R_3$ represents hydrogen, $C_1$-$C_6$alkyl, or benzyl;
$R_4$ represents
(ii) aryl, heterocyclic, aryl($C_1$-$C_6$alkyl)-, or heterocyclic($C_1$-$C_6$alkyl)-, any of which may be unsubstituted or substituted by cycloalkyl, non-aromatic heterocyclyl, methylenedioxy or any of the substituents defined as permitted in $R_{10}$; or
(ii) a radical of formula —(CR$_5$R$_6$)—Y—R$_7$ wherein
$R_5$ represents hydrogen, $C_1$-$C_6$alkyl, $C_2$-$C_6$alkenyl, $C_1$-$C_6$alkynyl, aryl, heteroaryl, cycloalkyl, aryl($C_1$-$C_6$alkyl)- or het roaryl($C_1$-$C_6$alkyl)-, any of which may be unsubstituted or substituted by any of the substituents defined as permitted in $R_{10}$
$R_6$ represents hydrogen or fluoro,
$R_7$ represents aryl, heteroaryl, —NH($C_1$-$C_6$alkyl), —N($C_1$-$C_6$alkyl)$_2$ or $C_1$-$C_6$alkyl, any of which may be unsubstituted or substituted by cycloalkyl, non-aromatic heterocyclyl, methylenedioxy or any of the substituents defined as permitted in $R_{10}$, and
Y represents a bond, —(CH$_2$)—, —C(=O)—, —C(=S)— or —C(=N—OR$_8$)— wherein $R_8$ represents $C_1$-$C_6$ alkyl or benzyl.

In another aspect, the invention provides a method for the treatment of bacterial or protozoal infections in humans and non-human mammals, which comprises administering to a subject suffering such infection an antibacterially or antiprotozoally effective dose of a compound of formula (I) as defined above.

In a further aspect of the invention there is provided a method for the treatment of bacterial contamination by applying an antibacterially effective amount of a compound of formula (I) as defined above to the site of contamination.

The compounds of formula (I) as defined above may be used as component(s) of antibacterial cleaning or disinfecting materials.

To the extent that compounds of formula (I) do not form part of the state of the art, such compounds and their pharmaceutically or veterinarily acceptable salts, hydrates or solvates are also an aspect of the present invention. In particular, the invention includes (a) compounds of formula (I) above wherein Z represents a radical of formula —N(OH)CH(=O), and $R_4$ represents aryl or heterocyclic, either of which may be unsubstituted or substituted by cycloalkyl, non-aromatic heterocyclyl, methylenedioxy or any of the substituents defined as permitted in $R_{10}$; and (b) compounds of formula (I) above wherein Z represents a radical of formula —N(OH)CH(=O), and $R_4$ represents aryl($C_1$-$C_6$alkyl)- or heterocyclic($C_1$-$C_6$alkyl)-, either of which may be unsubstituted or substituted by cycloalkyl, non-aromatic heterocyclyl, methylenedioxy or any of the substituents defined as permitted in $R_{10}$ EXCEPT THAT the —($C_1$-$C_6$alkyl)- radical in the aryl($C_1$-$C_6$alkyl)- or heteroaryl($C_1$-C6alkyl)-group may not be substituted by oxo; and (c) compounds of formula (I) above wherein Z represents a radical of formula —N(OH)CH(=O), and $R_4$ represents a radical of formula —(CR$_5$R$_6$)—Y—R$_7$ wherein
$R_5$ represents hydrogen, $C_1$-$C_6$alkyl, $C_2$-$C_6$alkenyl, $C_1$-$C_6$alkynyl, aryl, heteroaryl, cycloalkyl, aryl($C_1$-$C_6$alkyl)- or heteroaryl($C_1$-$C_6$alkyl)-, any of which may be unsubstituted or substituted by or any of the substituents defined as permitted in $R_{10}$
$R_6$ represents hydrogen or fluoro,
$R_7$ represents aryl, heteroaryl, or $C_1$-$C_6$alkyl, any of which may be unsubstituted or substituted by cycloalkyl, non-aromatic heterocyclyl, methylenedioxy or any of the substituents defined as permitted in $R_{10}$, and
Y represents —(CH$_2$)—, —C(=O)—, —C(=S)— or —C(=N—OR$_8$)— wherein $R_8$ represents $C_1$-$C_6$ alkyl or benzyl; and (d) compounds of formula (I) above wherein Z represents a radical of formula —N(OH)CH(=O), and $R_4$ represents a radical of formula —(CR$_5$R$_6$)—Y—R$_7$ wherein
$R_5$ represents hydrogen, $C_1$-$C_6$alkyl, $C_2$-$C_6$alkenyl, $C_1$-$C_6$alkynyl, aryl, heteroaryl, cycloalkyl, aryl($C_1$-

C$_6$alkyl)- or heteroaryl(C$_1$-C$_6$alkyl)-, any of which may be unsubstituted or substituted by or any of the substituents defined as permitted in R$_{10}$ R$_6$ represents hydrogen or fluoro, R$_7$ represents —NH(C$_1$-C$_6$alkyl), —N(C$_1$-C$_6$alkyl)$_2$ either of which may be unsubstituted or substituted by cycloalkyl, non-aromatic heterocyclyl, methylenedioxy or any of the substituents defined as permitted in R$_{10}$ and Y represents —(CH$_2$)—, —C(=O)—, —C(=S)— or —C(=N—OR$_8$)— wherein R$_8$ represents C$_1$-C$_6$ alkyl or benzyl PROVIDED THAT when R$_6$ is hydrogen then Y is not —C(=O)—.

On the hypothesis that the compounds (I) act by inhibition of intracellular PDF, the most potent antibacterial effect may be achieved by using compounds which efficiently pass through the bacterial cell wall. Thus, compounds which are highly active as inhibitors of PDF in vitro and which penetrate bacterial cells are preferred for use in accordance with the invention. It is to be expected that the antibacterial potency of compounds which are potent inhibitors of the PDF enzyme in vitro, but are poorly cell penetrant, may be improved by their use in the form of a prodrug, ie a structurally modified analogue which is converted to the parent molecule of formula (I), for example by enzymic action, after it has passed through the bacterial cell wall. The same is true in the case of protozoa.

As used herein the term "(C$_1$-C$_6$)alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

As used herein the term "divalent (C$_1$-C$_6$)alkylene radical" means a saturated hydrocarbon chain having from 1 to 6 carbon atoms and two unsatisfied valencies.

As used herein the term "(C$_2$-C$_6$)alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "divalent (C$_2$-C$_6$)alkenylene radical" means a hydrocarbon chain having from 2 to 6 carbon atoms, at least one double bond, and two unsatisfied valencies.

As used herein the term "C$_2$-C$_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4hexynyl and 5-hexynyl.

As used herein the term "divalent (C$_2$-C$_6$)alkynylene radical" means a hydrocarbon chain having from 2 to 6 carbon atoms, at least one triple bond, and two unsatisfied valencies.

As used herein the term "cycloalkyl" means a saturated alicyclic moiety having from 3-8 carbon atoms and includes, for example, cyclopropyl, cyclobutyl, cyclopentyl, cyclohexyl, cycloheptyl and cyclooctyl.

As used herein the term "cycloalkenyl" means an unsaturated alicyclic moiety having from 3-8 carbon atoms and includes, for example, cyclopropenyl, cyclobutenyl, cyclopentenyl, cyclohexenyl, cycloheptenyl and cyclooctenyl. In the case of cycloalkenyl rings of from 5-8 carbon atoms, the ring may contain more than one double bond.

As used herein the term "aryl" refers to a mono-or bi-cyclic carbocyclic aromatic group, and to groups consisting of two covalently linked mono-or bi-cyclic carbocyclic aromatic groups. Illustrative of such groups are phenyl, biphenyl and napthyl.

As used herein the unqualified term "heterocyclyl" or "heterocyclic" includes "heteroaryl" as defined below, and in particular means a 5-8 membered aromatic or non-aromatic heterocyclic ring containing one or more heteroatoms selected from S, N and O, and optionally fused to a benzyl or second heterocyclic ring, and the term includes, for example, pyrrolyl, furyl, thienyl, piperidinyl, imidazolyl, oxazolyl, thiazolyl, thiadiazolyl, thiazepinyl, pyrazolyl, pyridinyl, pyrrolidinyl, pyrimidinyl, morpholinyl, piperazinyl, indolyl, 1,4-dihydroquinolyl, 4H-chromenyl, and benzimidazolyl rings.

As used herein the term "heteroaryl" refers to a 5- or 6-membered aromatic ring containing one or more heteroatoms, and optionally fused to a benzyl or pyridyl ring; and to groups consisting of (a) two such monocyclic or fused rings which are covalently linked; or (b) one such a monocyclic or fused ring covalently linked to an aryl group. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4(([1,2,3]-thiadiazoly4-yl) phenyl and 5-isoxazol-3-ylthienyl.

As used herein the unqualified term "carbocyclyl" or "carbocyclic" refers to a 5-8 membered ring whose ring atoms are all carbon.

Unless otherwise specified in the context in which it occurs, the term "substituted" as applied to any moiety herein means substituted with up to four substituents, each of which independently may be (C$_1$-C$_6$)alkyl, phenyl, benzyl, (C$_1$-C$_6$)alkoxy, phenoxy, hydroxy, mercapto, (C$_1$-C$_6$) alkylthio, amino, halo (including fluoro, chloro, bromo and iodo), trifluoromethyl, cyano, nitro, oxo, —COOH, —CONH$_2$, —COR$^A$, —COOR$^A$, —NHCOR$^A$, —CONHR$^A$, —NHR$^A$, —NR$^A$R$^B$, or —CONR$^A$R$^B$ wherein R$^A$ and R$^B$ are independently a (C$_1$-C$_6$)alkyl group. In the case where "substituted" means substituted by benzyl, the phenyl ring thereof may itself be substituted with any of the foregoing, except phenyl or benzyl.

There are at least two actual or potential chiral centres in the compounds according to the invention because of the presence of asymmetric carbon atoms. The presence of several asymmetric carbon atoms gives rise to a number of diastereoisomers with R or S stereochemistry at each chiral centre. The invention includes all such diastereoisomers and mixtures thereof. Currently, the preferred stereoconfiguration of the carbon atom carrying the R$_2$ group is R; that of the carbon atom carrying the R$_1$ group (when asymmetric) is R.

In the compounds of formula (I) and (IA) as defined above:

when Z is a radical of formula —N(OH)CH(=O) R$_1$ is hydrogen, methyl or trifluoromethyl. When Z is a radical of formula —N(OH)CH(=O), R$_1$ is hydrogen, methyl, trifluoromethyl, hydroxy or amino. Hydrogen is currently preferred in both cases.

R$_2$ may be, for example:
optionally substituted C$_1$-C$_8$ alkyl, C$_3$-C$_6$ alkenyl, C$_3$-C$_6$ alkynyl or cycloalkyl;
phenyl(C$_1$-C$_6$ alkyl)-, phenyl(C$_3$-C$_6$ alkenyl)- or phenyl (C$_3$-C$_6$ alkynyl)- optionally substituted in the phenyl ring;

cycloalkyl(C₁-C₆ alkyl)-, cycloalkyl(C₃-C₆ alkenyl)- or cycloalkyl(C₃-C₆ alkynyl)- optionally substituted in the cycloalkyl ring;

heterocyclyl(C₁-C₆ alkyl)-, heterocyclyl(C₃-C₆ alkenyl)- or heterocyclyl(C₃-C₆ alkynyl)- optionally substituted in the heterocyclyl ring; or $CH_3(CH_2)_pO(CH_2)_q$— or $CH_3(CH_2)_pS(CH_2)_q$—, wherein p is 0, 1, 2 or 3 and q is 1, 2 or 3.

Specific examples of $R_2$ groups include methyl, ethyl, n- and iso-propyl, n- and iso-butyl, n-pentyl, iso-pentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, phenylpropyl, 4-chlorophenylpropyl, 4-methylphenylpropyl, 4-methoxyphenylpropyl, benzyl, 4-chlorobenzyl, 4-methylbenzyl, and 4-methoxybenzyl.

Presently preferred groups at $R_2$ are n-propyl, n-butyl, n-pentyl, and cyclopedtylmethyl.

$R_3$ may be, for example, hydrogen, methyl, ethyl or benzyl. Hydrogen is presently preferred.

$R_4$ may be, for example, a mono- or bicyclic- aryl or heterocyclic ring system such as phenyl, furanyl, pyrrolyl, thienyl, naphthyl, 1,4-dihydroquinolyl, quinolinyl, isoquinolinyl, cinnolinyl, imidazolyl, indolyl, thiazolyl, tetrazolyl, oxazolyl, 4H-chromenyl or chromenyl; any of which may be substituted as specified in the definition of R above, for example by methyl, trifluoromethyl, phenyl, cyclohexyl, cyclopentyl, amino, hydroxy, chloro, nitro, oxo, piperidinyl, furanyl, pyrrolyl, thienyl or (particularly in the case of a phenyl ring or a fused benzene ring) by methylenedioxy.

When $R_4$ is a radical of formula —$(CR_5R_6)$—Y—$R_7$, $R_5$ and $R_6$ may be hydrogen and $R_7$ may be any of those groups listed above for $R_4$.

Specific examples of compounds within or for use within the scope of the invention include those of the Examples herein:

Compounds of the invention wherein Z is a radical of formula —N(OH)CH(=O) may be prepared by deprotection of a compound of formula (II) or its sulfonyl analogue

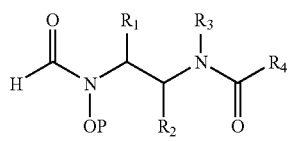
(II)

wherein P represents a hydroxy protecting group, and $R_1$, $R_2$, $R_3$ and $R_4$, are as defined in relation to formula (II). Compounds of formula (II) may be prepared by coupling an amine of formula (III),

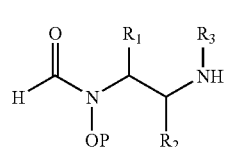
(III)

(IV)

with an acid of formula (I) wherein B is —(C=O)— or —(SO₂)— or an activated derivative thereof such as an acyl or sulfonyl chloride, using standard peptide coupling methods.

Compounds of formula (III) may be prepared by N-formylation, for example using formic acetic anhydride, or 1-formylbenzotriazole, of compounds of formula (IIIA)

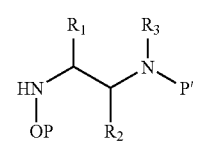
(IIIA)

Wherein P and P' represent hydroxy and amino protecting groups respectively, followed by removal of the amino protecting group P'.

Hydroxamate compounds of formula (I) for use in accordance with the invention may be prepared by reacting a compound of formula (V) or the sulfonyl analogue thereof, or a carboxyl-activated derivative thereof

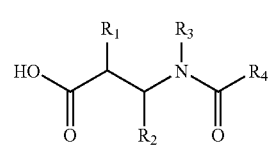
(V)

with hydroxylamine or an N- and/or O-protected hydroxylamine, and thereafter removing any O- or N-protecting groups. Carboxyl-activated derivatives of compound (V) include 1-hydroxybenzotriazole ester and pentafluorophenyl ester. A compound of formula (V) may be prepared by standard peptide coupling methods from an amine of formula (VI),

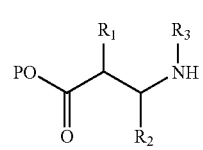
(VI)

wherein P is as defined in relation to formula (II), and an acid of formula (IV), followed by removal of P.

Intermediates of type (III), (IIIA), (IV) and (VI) are either commercially available or accessible by known chemistry from commercially available precursors. Further details of the synthetic routes available for use in the synthesis of the compounds with which the invention is concerned are given in the Examples herein.

Antibacterial or antiprotozoal compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the active ingredient(s) may be made up into a cream, lotion or ointment. Cream or ointment formulations which may be used for the drug are conventional formulations well known in the art, for example as described in standard textbooks of pharmaceutics such as the British Pharmacopoeia.

The active ingredient(s) may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle. Intra-venous infusion is another route of administration for the compounds used in accordance with the invention.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Specific examples of compounds of the invention include the following (where these compounds are N-formyl hydroxylamine derivatives, the corresponding hydroxamic acid analogues are also specific examples of compounds of the invention. Correspondingly where these compounds are hydroxamic acids the equivalent N-formyl hydroxylamine derivatives are also specific examples of compounds of the invention) examples 1-19.

The following abbreviations have been used throughout

| | |
|---|---|
| DIC | N,N-Dicyclohexylcarbodiimide |
| DIEA | Diisopropylethylamine |
| DMAP | N,N-Dimethylaminopyridine |
| DMF | Dimethylformamide |
| DPPA | Diphenylphosphoryl azide |
| ESMS | Electrospray mass spectroscopy |
| HOAt | 1-Hydroxy-7-aza-benzotriazole |
| HOBt | 1-Hydroxy-7-benzotriazole |
| HPLC | High performance liquid chromatography |
| LRMS | Low resolution mass spectrometry |
| NMR | Nuclear Magnetic Resonance |
| PyAOP | 7-Azabenzotriazol-1-yl-oxy-tris-pyrrolidino-phosphonium hexafluorophosphate |
| RT | Retention time |
| TBAF | Tetra-n-butyl ammonium fluorid |
| TFA | Trifluoroacetic acid |
| THF | Tetrahydrofuran |

$^1$H and $^{13}$C spectra were recorded using a Bruker DPX 250 spectrometer at 250.1 MHz (62.5 MHz for the $^{13}$C) and a Bruker AMX 500 spectometer at 500 MHz (125 MHz for the $^{13}$C). Mass spectra were obtained using a Perkin Elmer Sciex API 165. Analytical HPLC was run on a Beckman System Gold, using Waters Symmetry C18 column (50 mm, 4.6 mm) with 20 to 90% solvent B gradient (1.5 ml/min) as the mobile phase. [Solvent A: 0.05% TFA in 10% MeCN 90% water, Solvent B: 0.05% TFA in 10% water 90% MeCN, 5 min gradient time], detection wavelength at 220 or 214 nm. Preparative HPLC was run on a Gilson autoprep instrument using a C18 Waters delta pak (15□m, 300 Å, 25 mm, 10 mm) with 20 to 90% solvent B gradient as the mobile phase at a flow rate of 15 ml/min. [Solvent A 10% MeCN/water; Solvent B: 10% water/MeCN, 13 min gradient time], UV detection was at 220 or 214 nm. Reagents were purified and dried where necessary by standard techniques.

EXAMPLE 1

N-{1R-[(Formyl-hydroxy-amino)-methyl]-pentyl}2-naphthalen-1-yl-acetamide

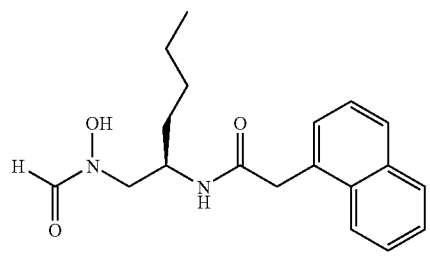

The title compound was prepared as detailed below (see Scheme 1) from 2R-[(Benzyloxy-formylamino)-methyl]-hexanoic acid, the synthesis of which has been described in WO 99/39704.

Scheme 1

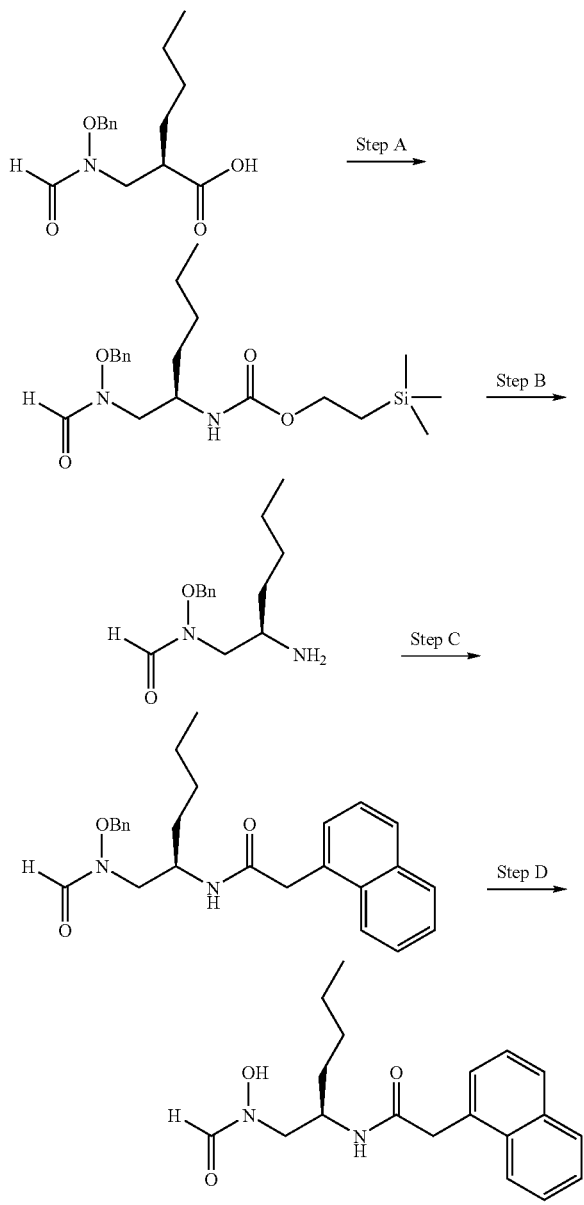

Reagents and conditions: A. DPPA, Et₃N, trimethylsilyl ethanol, toluene; B. TBAF, THF; C. PyAOP, HOAt, Et₃N, CH$_2$Cl$_2$; D. EtOH, H$_2$(g).

Step A: {1R-[(Benzyloxy-formyl-amino)-methyl]-pentyl}-carbamic acid 2-trimethylsilanyl-ethyl ester To a solution of 2R-[(benzyloxy-formylamino)-methyl]-hexanoic acid (0.5 g, 1.8 mmol) in toluene was added DPPA (379 µl, 1.8 mmol), and triethylamine (248 µl, 1.8 mmol). The reaction mixture was stirred at 80° C. under reflux for 0.5 h. Trimethylsilyl ethanol (516 µl, 3.6 mmol) was then added and the reaction mixture was stirred at 80° C. under reflux for 18 h. The mixture was allowed to cool and the solvent removed in vacuo to yield a clear oil. The residue was purified by flash chromatography (4:1, hexanes:ethyl acetate) to yield the title compound as a clear oil (882 mg, 62%). $^1$H-NMR; δ (CDCl$_3$, rotamers) 8.19 (1H, brs, CHO), 7.34 (5H, s, ArH), 4.83 (2H, brs), 4.72 (1H, brs), 4.13-4.10 (2H, m), 3.94 (1H, brm), 3.77 (1H, brm), 3.43 (1H, brm), 1.44-1.25 (6H, m), 0.93 (2H, t, J=8.5 Hz), 0.86-0.84 (3H, m), 0.00 (9H, s); LRMS: +ve ion 417 [M+Na, 100%]. HPLC RT: 7.0 min (100% @220 nm)

Step B: N-(2R-Amino-hexyl)-N-benzyloxy-formamide

To {1R-[(benzyloxy-formyl-amino)-methyl]-pentyl}carbamic acid 2-trimethylsilanyl-ethyl ester (200 mg, 0.51 mmol) was added a 1M solution of TBAF in THF (2.0 ml, 2.0 mmol), under a blanket of argon. The reaction mixture was stirred for 0.5 h at 50° C. and was then allowed to cool. The solvent was removed in vacuo, the resulting yellow oil was taken up in dichloromethane (20 ml), was washed with brine (1×20 ml), dried (anhydrous magnesium sulphate) and the solvent was evaporated to yield a clear oil, which was puirifed by flash chromatography (0.1M ammonia solution in MeOH 3%/dichloromethane) to yield the title compound as a white solid (98 mg, 77%). $^1$H-NMR; δ (CDCl$_3$, rotamers). 8.13 (0.7H, d, J=1.2 Hz), 8.00 (0.3H, d, J=11.9 Hz), 7.36-7.27 (5H, m, ArH), 5.75-5.71 (2H, m, NH$_2$), 4.69 (1.4H, s), 4.67 (0.6H, s), 4.22-4.09 (0.7H, m), 3.68-3.53 (0.3H, m), 3.11-2.65 (2H, m), 1.56-1.25 (6H, m), 0.92-0.86 (3H, m); LRMS +ve ion 251 [M+1, 100%], 273 [M+Na, 60%], HPLC RT: 4.5 min (100% @220nm)

Step C: N-{1R-[(Benzyloxy-formyl-amino)-methyl]-pentyl}2-naphthalen-1-yl-acetamide To a solution of N-(2R-amino-hexyl)-N-benzyloxy-formamide in dichloromethane (5 ml) was added 1-naphthyl acetic acid (70 mg, 0.38 mmol), PyAOP (232 mg, 0.45 mmol), HOAt (5 mg, 34.4 µmol) and triethylamine (95 µl, 0.69 mmol), the reaction mixture was stirred for 18 h at room temperature. The solvent was removed in vacuo and the crude yellow oil was taken up in ethyl acetate (30 ml) and was washed with 1M hydrochloric acid (1×30 ml), 1M sodium carbonate (1×30 ml), brine (1×30 ml), dried (anhydrous magnesium sulphate) and the solvent removed in vacuo to yield a clear oil, which was purified by flash chromatography (3.5% methanol/dichloromethane) to yield the title compound as a clear oil (86 mg, 60%). $^1$H-NMR; δ (CDCl$_3$, rotamers). 7.93-7.73 (4H, m, ArH, CHO), 7.50-7.24 (9H, m, ArH), 5.95 (1H, brs, NH), 4.88 (2H, dd, J=27.3 Hz & 10.8 Hz), 4.36 (1H, brs), 4.16-3.95 (3H, m), 3.46 (1H, dd, J=14.8 Hz & 4.4 Hz), 1.39-1.15 (6H, m), 0.85-0.81 (3H, m). LRMS +ve ion 419 (M+1, 40%), 441 (M+Na, 50%), HPLC RT: 6.5 min (100% @220 nm)

Step D: N-{1R-[(Formyl-hydroxy-amino)-methyl]-pentyl}-2-naphthalen-1-yl-acetamide To a solution of N{1R-[(benzyloxy-formyl-amino)-methyl]-pentyl}-2-naphthalen-1-yl-acetamide (86 mg, 0.20 mmol) in ethanol (5 ml), under a blanket of argon, was added 10% palladium on charcoal (10 mg) and a few drops of formic acid. Hydrogen was bubbled through the suspension for 1 hour and then the reaction was stirred under an atmosphere of hydrogen for 60 hours. The palladium catalyst was filtered off and the solvent removed in vacuo to yield a clear oil (60 mg) which was impure. The residue was purified by preparative HPLC to yield the title compound as a white solid (40 mg, 60%).

$^1$H-NMR; δ (CDCl$_3$), 8.99 (1H, s, CHO), 7.87 (1H, d, J=8.1 Hz), 7.81-7.77 (2H, m, ArH), 7.52-7.39 (3H, m, ArH), 7.28-7.25 (1 H, m, ArH), 6.20 (1 H, d, J=8.5 Hz, NH), 4:25(1H, d, J=16.6 Hz), 4.124.00 (2H, m), 3.99-3.91 (1H, m), 2.97 (1H, dd, J=2.8 Hz & 13.3 Hz), 1.45-1.00 (6H, m), 0.85 (3H, t, J=7.2 Hz); $^{13}$C-NMR; δ (CDCl$_3$), 14.2, 22.6, 28.5, 30.5, 36.7, 46.0, 50.9, 124.4, 125.9, 126.1, 128.1 (2c), 128.8, 129.1, 132.4, 132.8, 134.1, 164.0, 172.6; LRMS: +ve ion 329(M+1, 40%), 352 (M+Na, 100%), –ve ion 327(M–1, 100%) HPLC: RT 5.9 min (100% @220 nm).

Examples 2-5 were prepared from the common intermediate as shown in Scheme 2. The acid chloride of each right hand side fragment was used as the coupling partner rather than tradition coupling reagents. The acid chlorides were formed form the corresponding acid using thionyl chloride. These compounds were not isolated and were used directly in the coupling step (Scheme 2).

Step B: N-(2R-amino-hexyl)-N-hydroxy-formamide

To a solution of N-{1R-[(benzyloxy-formyl-amino)-methyl]-pentyl}2-naphthalen-1-yl-acetamide (5.5 g, 14.3 mmol) in ethanol (60 ml), under a blanket of argon, was added 10% palladium on charcoal (550 mg) in a slurry of EtOH (10 ml). Hydrogen was bubbled through the suspension for 2.5 h and then the reaction was stirred under an atmosphere of hydrogen for 60 hours. The palladium catalyst was filtered off and the solvent removed in vacuo to

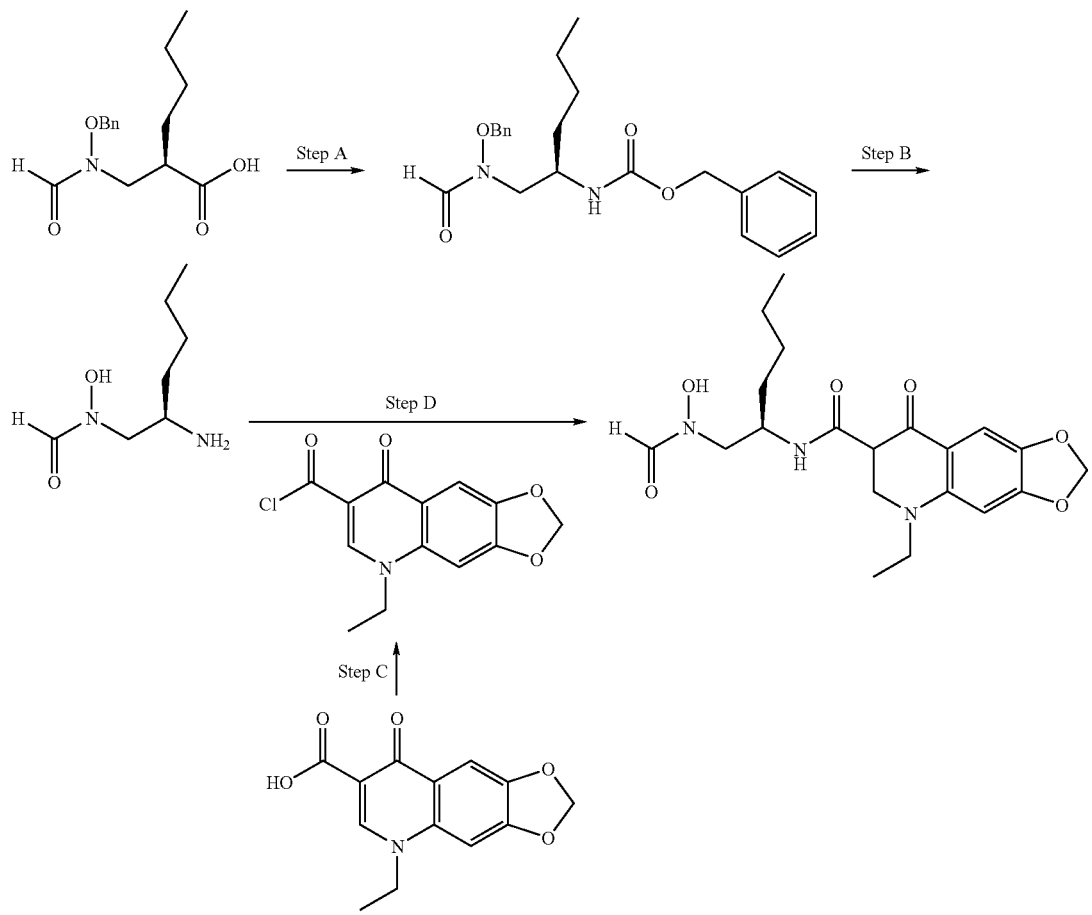

Scheme 2

Reagent and Conditions: Step A: DPPA, Et₃N, BnOH, toluene; Step B: H₂, Pd/C, EtOH; StepC: SOCl₂, CH₂Cl₂ 80° C.; Step D: CH₂Cl₂, acid chlorides, aminomethyl polystytene resin, DIEA resin.

Step A: {1R-[(Benzyloxy-formyl-amino)-methyl]-pentyl}carbamic acid benzyl ester

To a solution of 2R-[(Benzyloxy-formylamino)-methyl]-hexanoic acid (7.4 g, 26.5 mmol) in toluene (80 ml) was added DPPA (5.6 ml, 26.5 mmol), and triethylamine (3.7 ml, 26.5 mmol). The reaction mixture was stirred at 80° C. under reflux for 1 h. benzyl alcohol (5.7 ml, 53 mmol) was then added and the reaction mixture was stirred at 80° C. under reflux for 18 h. The mixture was allowed to cool and the solvent removed in vacuo to yield a clear oil. The residue was purified by flash chromatography (4:1, hexanes:ethyl acetate gradient to 1:1 hexanes:ethyl acetate) to yield the title compound as a clear oil (5.5 g, 54%). Compound was used directly in the next step without further purification. LRMS: +ve ion 385 (M+1), 407 (M+Na); HPLC RT: 6.5 min (80% @220 nm).

yield a clear oil (60 mg.) which was impure. The residue was purified by preparative HPLC to yield the title compound as a white solid (40 mg, 60%). LRMS: +ve ion: 161 (M+1).

Step C: 5-ethyl-8-oxo-5,8-dihydro-[1,3]dioxolo[4,5]quinoline-7-carboxylic acid chloride To a solution of 5-ethyl-8-oxo-5,8-dihydro-[1,3]dioxolo[4,5]quinoline-7-carboxylic acid (245 mg, 0.94 mmol) in dichloromethane (3 ml) was added thionyl chloride (2 ml) and the reaction mixture was stirred at 80° C. for 4 h. The mixture was allowed to cool and the solvent was removed in vacuo. The crude acid chloride was used directly in the coupling step without further purification.

Step D: 5-Ethyl-8-oxo-5,8-dihydro-[1,3]dioxolo[4,5]quinoline-7-carboxylic acid {1R-[(formyl-hydroxy-amino)-methyl]-pentyl}-amide.

To a solution of 5-ethyl-8-oxo-5,8-dihydro-[1,3]dioxolo[4,5]quinoline-7-carboxylic acid chloride (isolated crude from previous reaction) in dichloromethane (5 ml) was added a solution of N-(2R-amino-hexyl)-N-hydroxy-formamide (60 mg, 0.38 mmol) in dichloromethane (5 ml) followed by DIEA resin (1.44 g, 3.9 mmol/g), the suspension was stirred at room temperature for 24 h. Aminomethyl polystyrene resin (1.0 g, 1.5 mmol/g) was then added to the reaction mixture and the reaction mixture was stirred for a further 60 h. The resins were filtered and washed with dichloromethane (3×5 ml and methanol (3×5 ml), the filtrate was combined and the solvent was removed in vacuo to yield an impure oil. Preparative HPLC yielded the title compound (3.5 mg) as an oil. See table 1 for characterisation data.

Examples 2-5 were prepared in a manner analogous to example 1. Characterisation data for these compounds is shown in table 1. Also shown is there inhibition of the PDF *E. coli*(Ni) enzyme.

TABLE 1

| Example | Structure | | BB NUMBER | E coli PDF (Ni) (nM) | HPLC RT (min) | MS |
|---|---|---|---|---|---|---|
| 2 | 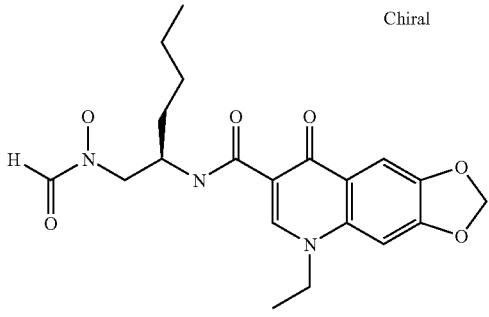 | Chiral | 85138 | 30 | 5.6 min (95%) | 404(M + 1) 426(M + Na) |
| 3 | 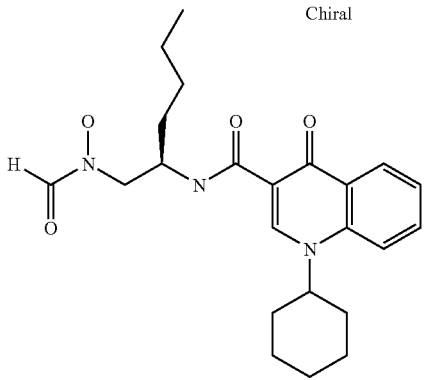 | Chiral | 85140 | 60 | 6.2 min (95%) | 414(M + 1) 436(M + Na) |
| 4 | 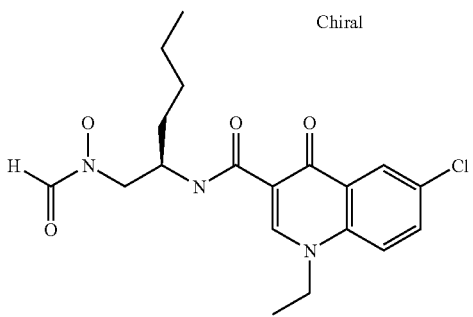 | Chiral | 85151 | 20 | 6.1 min (100%) | 416(M + Na) |

TABLE 1-continued

| Example | Structure | BB NUMBER | E coli PDF (Ni) (nM) | HPLC RT (min) | MS |
|---|---|---|---|---|---|
| 5 | Chiral | 85152 | 200 | 5.8 min (96%) | 332(M + 1) 355(M + Na) 331(M − 1) |

2. 5-Ethyl-8-oxo-5,8-dihydro-[1,3]dioxolo[4,5]quinoline-7-carboxylic acid {1R-[(formyl-hydroxy-amino)-methyl]-pentyl}amide.

3. 1-Cyclohexyl-4-oxo-1,4-dihydro-quinoline-3-carboxylic acid {1R[(formyl-hydroxy-amino)-methyl]-pentyl}-amide.

4. 6-Chloro-1-ethyl-4-oxo-1,4-dihydro-quinoline-3-carboxylic acid {1R[(formyl-hydroxy-amino)-methyl]-pentyl}-amide.

5. 4-Oxo-4H-chromene-3-carboxylic acid {1R-[(formyl-hydroxy-amino)-methyl]-pentyl}amide.

EXAMPLE 6

3-(Naphthalene-1-sulfonylamino)-hexanoic acid hydroxyamide

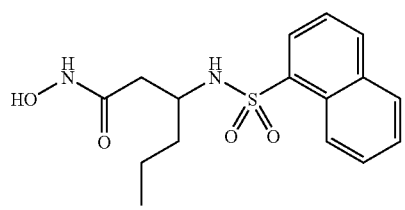

The title compound was prepared as described below:

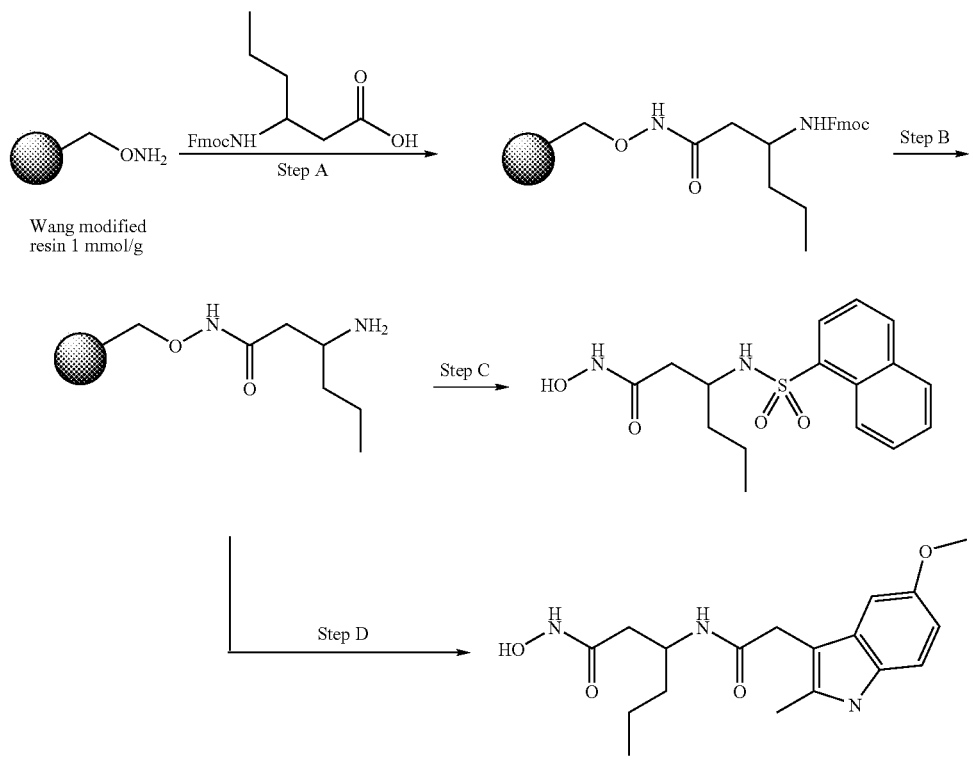

Reagents and conditions: A. Fmoc-β-3-aminohexanoic acid, HOBT, DIC, DMF, O/N; B. 20% piperazine, DMF, 5 h; C. (I) methyl trimethyl allyl dimethyl ketone acetal, DMAP, 1-naphthalene sulphonylchloride, $CH_2Cl_2$ and (ii) 1:9:10 Trimethyl silane/trifluoroacetic acid/$CH_2Cl_2$; D. (I) DIC, 5-methoxy-2-methyl-3-indole acetic acid, DMF and (ii) 1:9:10 Trimethyl silane/trifluoroacetic acid/$CH_2Cl_2$ Note: For the preparation of Wang modified resin see C. Floyd et al., Tetrahedron Left., 1996, 37, 8045.

Step A: Fmoc-beta-3-aminohexanoyl-p-benzyloxybenzyl alcohol resin hydroxamate

To a solution of Fmoc-β-3aminohexanoic acid (2.12 g, 6.0 mmol), HOBT (0.81 g, 6.0 mmol) and DIC (0.67 ml, 6.0 mmol) in DMF (20 ml) was added p-benzyloxybenzyl alcohol resin (2.0 g, 2.0 mmol). The reaction mixture was shaken overnight. The resin was filtered and washed with DMF (3×10 ml). The resin was then washed with MeOH (10 ml) followed by dichloromethane (10 ml) and this process was repeated three times. The resin was dried overnight under reduced pressure.

Step B: Beta-3-aminohexanoyl-p-benzyloxybenzyl alcohol resin hydroxamate

A 20% solution of piperazine in DMF (20 ml) was added to Fmoc-β-3-aminohexanoyl-p-benzyloxybezyl alcohol resin hydroxamate (2.59 g, 2 mmol). The reaction mixture was shaken for 5 hours. The resin was filtered and washed with DMF (3×10 ml). The resin was then washed with MeOH (10 ml) followed by dichloromethane (10 ml) and this process was repeated three times. The resin was dried overnight under reduced pressure.

Step C: 3-(Naphthalene-1-sulfonylamino)-hexanoic acid hydroxyamide (i) A solution of methyl trimethyl allyl dimethyl ketone acetal (304 μl, 1.5 mmol) and DMAP (3.8 mg, 0.03 mmol) in dichloromethane (3 ml) was added to β-3-aminohexanoyl-p-benzyloxybenzyl alcohol resin hydroxamate (150 mg, 0.15 mmol) followed by the addition of 1-naphthalene sulphonylchloride (340 mg, 1.5 mmol). The reaction mixture was shaken overnight. The resin was filtered and washed with DMF (3×10 ml). The resin was then washed with MeOH (10 ml) followed by dichloromethane (10 ml) and this process was repeated three times. The resin was dried overnight under reduced pressure.

(ii) A solution of 1:4:5 trimethylsilane/trifluoroacetic acid/dichloromethane (3 ml) was added to 3-(Naphthalene-1-sulfonylamino)-hexanoyl-p-benzyloxybenzyl alcohol resin hydroxamate (170 mg, 0.15 mmol). The reaction mixture was stirred occasionally over 45 minutes. The solution was collected by filtration and the resin washed with a solution of 1:4:5 trimethylsilane/trifluoroacetic acid/dichloromethane (2 ml) and dichloromethane (3 ml). The solvents were removed under reduced pressure and the residue was purified by preparative HPLC. The title compound was obtained as a clear oil (1.9 mg, 4%). Characterisation data is provided in Table 2.

Step D: 3-[2-(5-Methoxy-2-methyl-1H-indol-3-yl)-acetylamino]-hexanoic acid hydroxyamide (i) To a solution of 5-methoxy-2-methyl-3-indole acetic acid (98 mg, 0.45 mmol) and DIC (70 □l, 0.45 mmol) in DMF, was added β-3-[2-(5-methoxy-2methyl-1H-indol-3-yl)-acetylamino]-hexanoyl-p-benzyloxybenzyl alcohol resin hydroxamate. The reaction mixture was shaken overnight. The resin was filtered and washed with DMF (3×10 ml) once followed by washes with MeOH (10 ml) then dichloromethane (10 ml) repeated three times. The resin was dried overnight under reduced pressure.

(ii) A solution of 1:4:5 trimethylsilane/trifluoroacetic acid/dichloromethane (3 ml) was added to β-3-[2-(5-methoxy-2-methyl-1H-indol-3-yl)-acetylamino]-hexanoyl-p-benzyloxybenzyl alcohol resin hydroxamate (170 mg, 0.15 mmol). The reaction mixture was stirred occasionally over 45 min. The solution was collected by filtration and the resin washed with a solution of 1:4:5 trim thyl ilane/trifluoroacetic acid/dichloromethane (2 ml) and dichloromethane (3 ml). The solvent were removed under reduced pressure and the residue was purified by preparative HPLC. The title compound was obtained as a clear oil (11.8 mg, 22%). Characterisation data is provided in Table 2.

The compounds of Examples 6-19 were prepared by the synthetic route outlined in Scheme 2 and as described in detail for Example 6. Examples 7 8, 13, 14 and 15 were prepared as in scheme 3 but following Step C. Examples 9-12 and 16-19 were prepared as in scheme 3 but following Step D. Note: Examples 13-19 were prepared in a identical manner as shown in scheme 2 but utilising the starting material L-homoisoleucine. Compounds 6-19 were purified by preparative HPLC.

TABLE 2

| Example | Structure | ES-MS Ions Seen | Prep HPLC Retention Time (mins) |
|---|---|---|---|
| 6 | 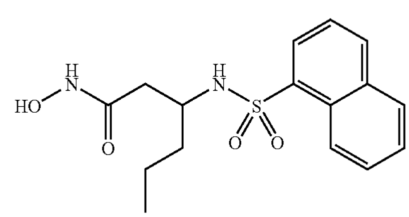 | M + Na = 359<br>M − 1 = 335 | 10.8 |

TABLE 2-continued

| Example | Structure | ES-MS Ions Seen | Prep HPLC Retention Time (mins) |
| --- | --- | --- | --- |
| 7 | 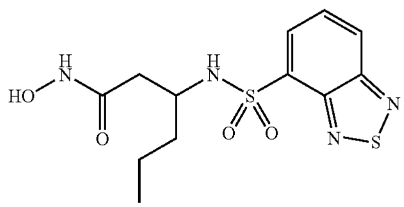 | M + Na = 367<br>M − 1 = 343 | 9.2 |
| 8 | 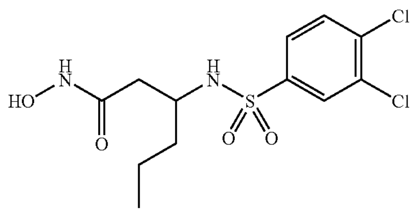 | M + Na = 377<br>M − 1 = 353 | 11.3 |
| 9 | 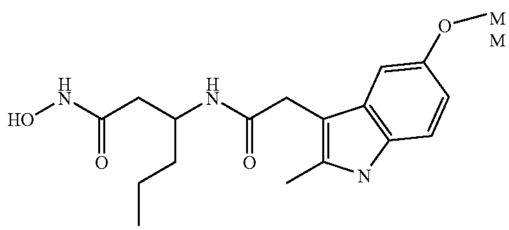 | M + 1 = 348<br>M − 1 = 346 | 9.6 |
| 10 | 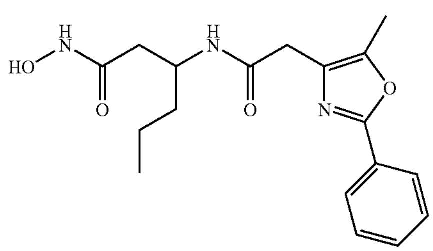 | M + Na = 368<br>M − 1 = 344 | 10.3 |
| 11 | 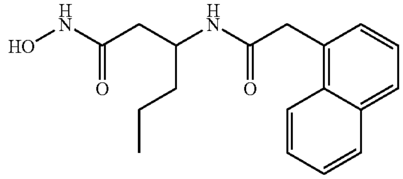 | M + Na = 337<br>M − 1 = 313 | 10.7 |
| 12 | 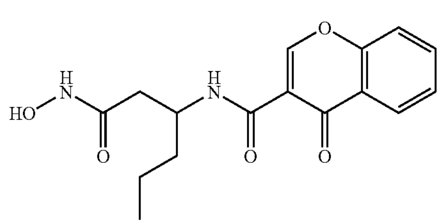 | M + Na = 341<br>M − 1 = 317 | 10.1 |

Examples 7-12 are named as follows:

EXAMPLE 7

3-(Benzo[1,2,5]thiadiazole4-sulfonylamino)-hexanoic acid hydroxyamide

EXAMPLE 8

3-(3,4Dichloro-benzenesulfonylamino)-hexanoic acid hydroxyamide

EXAMPLE 9

3-[2-(5-Methoxy-2-methyl-1 H-indol-3-yl)-acetylamino]-hexanoic acid hydroxyamide

EXAMPLE 10

3-[2-(5-Methyl-2-phenyl-oxazol-4-yl)-acetylamino]-hexanoic acid hydroxyamide

EXAMPLE 11

3-(2-Naphthalen-1-yl-acetylamino)-hexanoic acid hydroxyamide

EXAMPLE 12

4-Oxo-4H-chromene-3-carboxylic acid (1-hydroxycarbamoylmethyl-butyl)-amide

TABLE 3

| Example | Structure | ES-MS Ions Seen | Prep HPLC Retention Time (mins) |
|---|---|---|---|
| 13 | 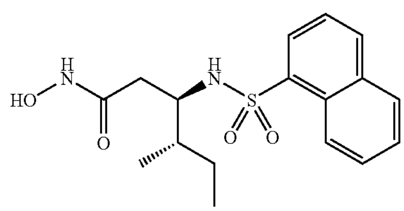 | M + Na = 373<br>M − 1 = 349 | 11.1 |
| 14 | 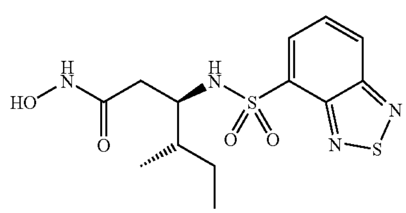 | M + Na = 381<br>M − 1 = 357 | 9.6 |
| 15 | 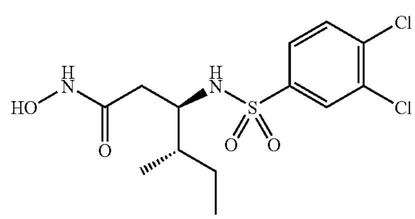 | M + Na = 391<br>M − 1 = 369 | 11.6 |
| 16 | 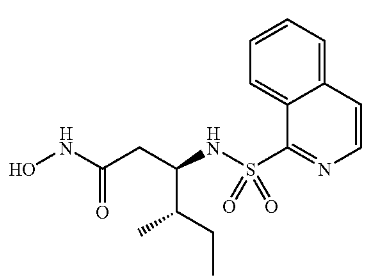 | M + 1 = 316<br>M − 1 = 314 | 10.3 |

TABLE 3-continued

| Example | Structure | ES-MS Ions Seen | Prep HPLC Retention Time (mins) |
|---|---|---|---|
| 17 | 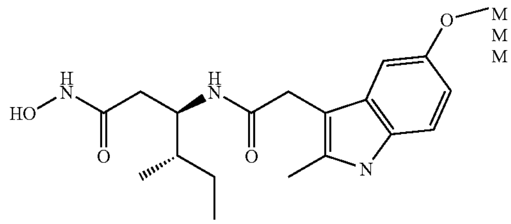 | M + H = 362<br>M + Na = 384<br>M − 1 = 3360 | 9.8 |
| 18 | 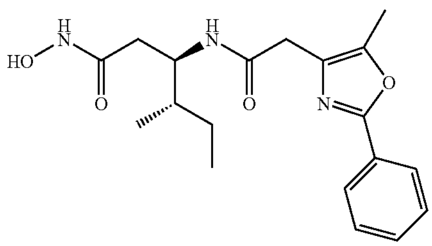 | M + Na = 337<br>M − 1 = 313 | 10.14 |
| 19 | 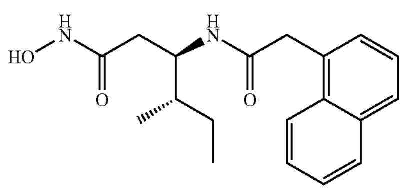 | M + Na = 351<br>M − 1 = 327 | 10.9 |

Examples 13-19 are named as follows:

EXAMPLE 13

4S-Methyl-3R-(naphthalene-1-sulfonylamino)-hexanoic acid hydroxyamide

EXAMPLE 14

3R-(Benzo[1,2,5]thiadiazole-4S-sulfonylamino)-methyl-hexanoic acid hydroxyamide

EXAMPLE 15

3R-(3,4-Dichloro-benzenesulfonylamino)-4S-methyl-hexanoic acid hydroxyamide

EXAMPLE 16

3R-(Isoquinoline-1-sulfonylamino)-4S-methyl-hexanoic acid hydroxyamide

EXAMPLE 17

3R-[2-(5-Methoxy-2-methyl-1H-indol-3-yl)-acetylamino]-4S-methyl-hexanoic acid hydroxyamide

EXAMPLE 18

4S-Methyl-3R-[2-(5-methyl-2-phenyl-oxazol4-yl)-acetylamino]-hexanoic acid hydroxyamide

EXAMPLE 19

4S-Methyl-3R-(2-naphthalen-1-yl-acetylamino)-methyl-hexanoic acid hydroxyamide

BIOLOGICAL EXAMPLE

The susceptibilities of strains of bacteria to the compound of Example 1 were determined by a standard agar plate dilution method following recommendations in British Society for Antimicrobial Chemotherapy Working Party. 1991, "A guide to sensitivity testing British Society for Antimicrobial Chemotherapy, London, United Kingdom". Briefly, Iso-Sensitest agar (pH 7.2: Oxoid, United Kingdom) is employed, supplemented with 5% horse blood (Oxoid) and 20 μg of NAD (Sigma) per ml are added to support growth of fastidious bacteria. The inoculum used is approximately $10^4$ colony forming units of each isolate contained in a volume of 1 μl. Plates are incubated 18 to 24 hr in air, or for fastidious bacteria an atmosphere enriched with 4-6% carbon dioxide at 35° C. The MIC is determined as the lowest concentration of an Antimicrobial tested that inhibited growth of the inoculum, disregarding a single persisting colony or faint haze caused by the inoculation.

The MICs of the compound against 3 test strains of Haemophilia influenza were in the range 0.5- 2 μg/ml.

The invention claimed is:

1. A compound of formula (I) or (IA) or a pharmaceutical or veterinarily acceptable salt, thereof:

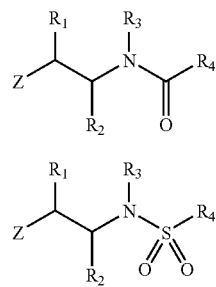

wherein:

Z represents a radical of formula —N(OH)CH(=O);

$R_1$ represents hydrogen, methyl or trifluoromethyl;

$R_2$ represents a radical of formula $R_{10}$—$(X)_n$—$(ALK)_m$— wherein $R_{10}$ represents hydrogen, or a $C_1$-$C_6$ alkyl, $C_2$-$C_6$ alkenyl, $C_2$-$C_6$ alkynyl, cycloalkyl, aryl, or heterocyclyl group, any of which may be unsubstituted or substituted by $(C_1$-$C_6)$ alkyl, $(C_1$-$C_6)$alkoxy, hydroxy, mercapto, $(C_1$-$C_6)$alkylthio, amino, halo, trifluoromethyl, cyano, intro, oxo, —COOH, —CONH$_2$, —COOR$^A$, —NHCOR$^A$, —NR$^A$COR$^B$, —CONHR$^A$, —NHR$^A$, —NR$^A$R$^B$ or —CONR$^A$R$^B$ wherein R$^A$ and R$^B$ are independently a $(C_1$-$C_6)$ alkyl group or R$^A$ and R$^B$ taken together with the atom(s) to which they are attached form a 5, 6 or 7 membered ring; and ALK represents a straight or branched divalent $C_1$-$C_6$ alkylene, $C_2$-$C_6$ alkenylene, or $C_2$-$C_6$ alkynylene radical, and may be interrupted by one or more non-adjacent —NH—, —O— or —S— linkages, X represents —NH—, —O— or —S—, and m and n are independently 0 or 1;

$R_3$ represents hydrogen, $C_1$-$C_6$alkyl, or benzyl;

$R_4$ represents
(a) aryl or heterocyclic, either of which may be unsubstituted or substituted by cycloalkyl, non aromatic heterocyclyl, methylenedioxy or any of the substituents defined as permitted in $R_{10}$; or
(b) aryl $(C_1$-$C_6$alkyl)- or heterocyclic($C_1$-$C_6$alkyl)-, either which may be unsubstituted or substituted by cycloalkyl, non-aromatic heterocyclyl, methylenedioxy or any of the substituents defined as permitted in $R_{10}$, EXCEPT THAT the $(C_1$-$C_6$alkyl)- radical in the aryl $(C_1$-$C_6$alkyl)- or heterocyclic($C_1$-$C_6$alkyl)- may not be substituted oxo.

2. The compound of claim 1 wherein $R_1$ is hydrogen.

3. The compound of claim 1 wherein $R_2$ is:

$C_1$-$C_8$ alkyl, $C_3$-$C_6$ alkenyl, $C_3$-$C_6$ alkynyl or cycloalkyl;

phenyl $(C_1$-$C_6$alkyl)-, phenyl $(C_3$-$C_6$ alkenyl)-or phenyl $(C_3$-$C_6$ alkynyl)- in the phenyl ring;

cycloalkyl($C_1$-$C_6$ alkyl)-, cycloalkyl($C_3$-$C_6$ alkenyl)- or cycloalkyl($C_3$-$C_6$ alkynyl)- in the cycloalkyl-ring;

heterocyclyl $(C_1$-$C_6$ alkyl)-, heterocyclyl $(C_3$-$C_6$ alkenyl)- or heterocyclyl $(C_3$-$C_6$ alkynyl)- in the heterocyclyl ring; or $CH_3(CH_2)_pO$ $(CH2)_q$ or $CH_3(CH_2)_pS(CH_2)_q$—, wherein p is 0, 1, 2 or 3 and q is 1, 2 or 3.

4. The compound of claim 1 wherein $R_2$ is methyl, ethyl, n- or iso-propyl, n- or iso-butyl, n-pentyl, iso-pentyl, 3-methyl-but-1-yl, n-hexyl, n-heptyl, n-acetyl, n-octyl, methylsulfanylethyl, ethylsulfanylmethyl, 2-methoxyethyl, 2 ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2ylmethyl, phenylpropyl, 4-chlorophenylpropyl, 4-methylphenylpropyl, 4methoxyphenylpropyl, benzyl, 4-chlorobenzyl, 4-methylbenzyl, or 4methoxybenzyl.

5. The compound of claim 1 wherein $R_2$ is n-propyl, n-butyl, n-pentyl, or cyclopentylmethyl.

6. The compound of claim 1 wherein $R_3$ is hydrogen.

7. The compound of claim 1 wherein $R_4$ is phenyl, furanyl, pyrrolyl, thienyl, naphthyl, quinolinyl, isoquinolinyl, cinnolinyl, imidazolyl, indolyl, thiazolyl, tetrazolyl, oxazolyl, quinolyl, 1,4-dihydroquinolyl, 4H-chromenyl or chromenyl, any of which may be substituted by methyl, trifluoromethyl, phenyl, ammo, hydroxy, chloro, nitro, oxo, piperidinyl, furanyl, pyrrolyl, thienyl or (in the case of a phenyl ring or a fused benzene ring) by methylenedioxy.

8. The compound of claim 7 wherein $R_1$ and $R_3$ are hydrogen, and $R_2$ is n-propyl, n-butyl, n-pentyl, or cycopentylmethyl.

9. A pharmaceutical or veterinary composition comprising a compound as claimed in claim 1 together with a pharmaceutically or veterinarily acceptable carrier.

* * * * *

UNITED STATES PATENT AND TRADEMARK OFFICE
CERTIFICATE OF CORRECTION

PATENT NO. : 7,323,596 B2  
APPLICATION NO. : 10/433625  
DATED : January 29, 2008  
INVENTOR(S) : Barry Porter et al.

Page 1 of 1

It is certified that error appears in the above-identified patent and that said Letters Patent is hereby corrected as shown below:

In Column 29, Claim 1, Line 33:
    Please delete "intro" and insert --nitro--.

Signed and Sealed this

Second Day of December, 2008

JON W. DUDAS  
*Director of the United States Patent and Trademark Office*